United States Patent [19]

Kelly et al.

[11] Patent Number: 5,250,222
[45] Date of Patent: Oct. 5, 1993

[54] OPTICALLY ACTIVE COMPOUNDS USED FOR LIQUID CRYSTALLINE MIXTURES

[75] Inventors: Stephen Kelly, Möhlin; Frans Leenhouts, Kaiseraugst; Alois Villiger, Basel, all of Switzerland

[73] Assignee: Hoffmann-La Roche Inc., Nutley, N.J.

[21] Appl. No.: 866,076

[22] Filed: Apr. 1, 1992

Related U.S. Application Data

[63] Continuation of Ser. No. 758,245, Sep. 10, 1991, abandoned, which is a continuation of Ser. No. 234,222, Aug. 19, 1988, abandoned.

[30] Foreign Application Priority Data

Aug. 25, 1987 [CH] Switzerland ............ 3245/87
Jul. 7, 1988 [CH] Switzerland ............ 2593/88

[51] Int. Cl.$^5$ ............... C09K 19/12; C07C 41/00
[52] U.S. Cl. ............... 252/299.66; 568/631;
252/299.61; 252/299.63; 252/299.65;
252/299.67
[58] Field of Search ........... 252/299.01, 299.6, 299.63,
252/299.61, 299.64, 299.65, 299.66, 299.67;
568/631

[56] References Cited

U.S. PATENT DOCUMENTS

| | | |
|---|---|---|
| 4,264,148 | 4/1981 | Gobl-Wunsch et al. |
| 4,265,600 | 3/1987 | Heppke et al. |
| 4,296,631 | 10/1981 | Fergason |
| 4,753,752 | 6/1988 | Raynes et al. ............ 252/299.65 |
| 4,780,240 | 10/1988 | Emoto et al. ............ 252/299.66 |
| 4,834,904 | 5/1989 | Krause et al. ............ 252/299.61 |
| 5,064,569 | 11/1991 | Geelhaar et al. ............ 252/299.65 |

FOREIGN PATENT DOCUMENTS

| | | |
|---|---|---|
| 0211646 | 2/1987 | European Pat. Off. |
| 0269062 | 6/1988 | European Pat. Off. ....... 252/299.65 |
| 3534778 | 4/1987 | Fed. Rep. of Germany |
| 3534780 | 4/1987 | Fed. Rep. of Germany |
| 3617826 | 4/1987 | Fed. Rep. of Germany |

PCT/DE870-0035 8/1987 PCT Int'l Appl. ............. 252/299.6

OTHER PUBLICATIONS

Patent Abstract of Japan, vol. 12, No. 459 (C-547) 3297, Nov. 25, 1988, p. 75 C 547 Corresponding to JP application Ser. No. 63-175095.
Patent Abstract of Japan, vol. 13, No. 233 (C-601) 3581, May 29, 1989, p. 81 C 601 Corresponding to JP application Ser. No. 1-42454.
Derwent Abstract 80-05545C/04 corresponds to DE 2827471.

*Primary Examiner*—Philip Tucker
*Attorney, Agent, or Firm*—George M. Gould; George W. Johnston

[57] ABSTRACT

Optically active compounds of the formula

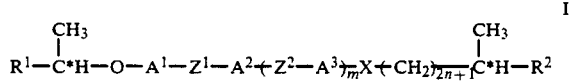

wherein $R^1$ and $R^2$ each are alkyl with at least 2 carbon atoms; $A^1$, $A^2$ and $A^3$ each are unsubstituted, cyano-, halogen- or methyl-substituted 1,4-phenylene, optionally having one or two CH groups replaced by nitrogen, unsubstituted, cyano- or methyl-substituted trans-1,4-cyclohexylene, the cyclohexylene optionally having one or two $CH_2$ groups replaced by oxygen; $Z^1$ and $Z^2$ each are a single covalent bond, —COO—, —OOC—, —$CH_2CH_2$—, —$OCH_2$—, —$CH_2O$—, —C≡C—, —COS— or —SOC—; m stands for the number 0 or 1; n is an integer of 0 to 4; X is oxygen or a methylene group; and each C* represents a chiral carbon atom, one of the chiral carbon atoms has the R-configuration while the other has the S-configuration.

The compounds are used in liquid crystalline mixtures to compensate the temperature dependence of the threshold potential of liquid crystal cells.

9 Claims, No Drawings

OPTICALLY ACTIVE COMPOUNDS USED FOR LIQUID CRYSTALLINE MIXTURES

This is a continuation of application Ser. No. 07/758,245 filed Sep. 10, 1991, now abandoned, which is a continuation of copending application Ser. No. 07/234,222 filed on Aug. 19, 1988, now abandoned.

FIELD OF THE INVENTION

The present invention is concerned with novel optically active compounds and their use for electro-optical purposes as well as with liquid crystalline mixtures and liquid crystal cells which contain these compounds.

BACKGROUND OF THE INVENTION

It is known that the optical characteristics of liquid crystal cells are temperature-dependent. For example, the threshold potential of twisted nematic liquid crystal displays (usually abbreviated to TN-LCD) decreases with increasing temperature. This dependence is disadvantageous above all for multiplex applications.

On the other hand, liquid crystal materials for TN-LCDs are frequently treated with an optically active component in order to avoid the reversal of the twisting direction ("reverse twist"). The threshold potential $V^p_{th}$ of TN-LCDs when such a material doped with an optically active component is used may be approximated from the following equation:

$$V^p_{th} \approx V^0_{th}(1+F\cdot d/|p|)^{\frac{1}{2}} \qquad (1)$$

in which $V^0_{th}$ denotes the threshold potential when the undoped material is used, d is the plate separation (that is, the layer thickness of the liquid crystal material), $|p|$ denotes the absolute value of the natural pitch of the doped liquid crystal material and F is a function of the elastic contants and the twisting in the cell [Appl. Phys. Lett. 25, 12 (1974) and IEEE Trans. Electron Devices ED-10, 141 (1974)].

From equation (1) it follows that the decrease in the threshold potential can be compensated for wholly or partially by using optically active doping materials which induce a decreasing absolute value of the pitch p with increasing temperature, similar considerations also apply to liquid crystal cells such as STN-LCDs ("supertwisted nematic"), SBE-LCDs ("supertwisted birefringence effect"), OMI-LCDs ("optical mode interference") and the like.

From DE-A-2827471, Z. Naturforschung 34a, 594 (1979) and Phys. Lett. 78A., 285 (1980) it is known that a decreasing value of $|p|$ with increasing temperature can be achieved by adding at least two suitable, optically active doping materials in a fixed ratio insofar as one of the doping materials in the nematic carrier substance produces a right-handed twisting and the other produces a left-handed twisting. However, such a doping has the disadvantage that two or more optically active doping materials are required and in general even small deviations in the ratio lead to large variations in the temperature pattern of the threshold potential and the pitch. Moreover, relatively high total concentrations of doping materials are usually required.

However, only few individual compounds having the desired property are known and the decrease of $|p|$ with increasing temperature is limited as a rule to a narrow or unfavourable temperature range, whereby the display quality or the utilizable temperature range is distinctly reduced. EP-A-0211646 discloses, for example, compounds having two similar centers of chirality, which have the desired temperature dependence above 0° C., but which lead to helix inversion between about −20° C. and 0° C.

SUMMARY OF THE INVENTION

The invention is concerned with optically active compounds of the formula

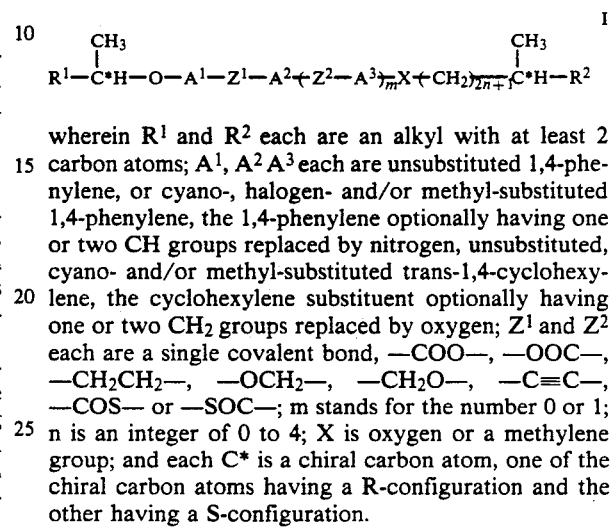

wherein $R^1$ and $R^2$ each are an alkyl with at least 2 carbon atoms; $A^1$, $A^2$ $A^3$ each are unsubstituted 1,4-phenylene, or cyano-, halogen- and/or methyl-substituted 1,4-phenylene, the 1,4-phenylene optionally having one or two CH groups replaced by nitrogen, unsubstituted, cyano- and/or methyl-substituted trans-1,4-cyclohexylene, the cyclohexylene substituent optionally having one or two $CH_2$ groups replaced by oxygen; $Z^1$ and $Z^2$ each are a single covalent bond, —COO—, —OOC—, —$CH_2CH_2$—, —$OCH_2$—, —$CH_2O$—, —C≡C—, —COS— or —SOC—; m stands for the number 0 or 1; n is an integer of 0 to 4; X is oxygen or a methylene group; and each C* is a chiral carbon atom, one of the chiral carbon atoms having a R-configuration and the other having a S-configuration.

The compounds of formula I have the desired temperature dependence of the pitch in the entire temperature range which is usually required for commercial applications, especially in the range of about −30° C. to +80° C. They frequently have liquid crystalline properties themselves, are chemically stable and have a good miscability with known liquid crystal materials. The compounds of formula I are therefore useful in modifying the temperature dependence of the pitch, and are especially useful for compensating the temperature dependence of the threshold potential.

DETAILED DESCRIPTION OF THE INVENTION

The terms "chiral carbon atom having a R-configuration" and "chiral carbon atom having a S-configuration" refer to the conventional R/S nomenclature for chiral compounds.

Formula I above embraces not only compounds in which $R^1$—C*H($CH_3$)—O— has the R-configuration and —X—$(CH_2)_{2n+1}$—C*H($CH_3$)—$R^2$ has the S-configuration, but also their optical antipodes in which $R^1$—C*H($CH_3$)—O— has the S-configuration and —X—$(CH_2)_{2n+1}$—C*H($CH_3$)—$R^2$ has the R-configuration. Both of the optical isomers have the same properties, but with opposite helix direction of rotation, opposite optical rotation signs etc.

The term "alkyl with at least 2 carbon atoms" embraces straight-chain and branched alkyl groups such as ethyl, propyl, isopropyl, butyl, isobutyl, 2-methylbutyl, pentyl, hexyl, heptyl, octyl, nonyl, decyl and the like. Groups with 2 to 10 carbon atoms are generally preferred.

The term "halogen" embraces fluorine, chlorine, bromine and iodine, preferably fluorine and chlorine.

The term "unsubstituted, cyano-, halogen- and/or methyl-substituted 1,4-phenylene, optionally having one or two CH groups replaced by nitrogen," embraces 1,4-phenylene, pyridine-2,5-diyl, pyrazine-2,5-diyl.

pyrimidine-2,5-diyl and pyridazine-3,6-diyl as well as substituted rings derived therefrom such as 2-methyl-1,4-phenylene, 2-fluoro-1,4-phenylene, 2-cyano-1,4-phenylene, 2,3-dicyano-1,4-phenylene and the like.

The term "unsubstituted, cyano- and/or methyl-substituted trans-1,4-cyclohexylene, optionally having one or two $CH_2$ groups replaced by oxygen," embraces rings such as trans-1,4-cyclohexylene, trans-1,3-dioxane-2,5-diyl as well as substituted rings derived therefrom such as 2-methyl-trans-1,4-cyclohexylene, 1-cyano-trans-1,4-cyclohexylene and the like.

The decrease in the pitch $|p|$ with increasing temperature is based principally on the presence of the terminal groups $R^1$—$C^*H(CH_3)$—O— and —X—$(CH_2)_{2n+1}$—$C^*H(CH_3)$—$R^2$, especially on the relative configuration and on the position of the chiral carbon atoms. Variations in the central group have as a rule only a slight influence on the temperature dependence of the pitch. The central group —$A^1$—$Z^1$—$A^2$—$(Z^2$—$A^3$—$)_m$ in formula I can therefore have the above-named rings and bridging groups which are usual in liquid crystals without essentially influencing the desired effect. On the other hand, depending on the choice of rings and bridging groups other properties such as the mesophase, dielectric anisotropy, viscosity, optical anisotropy and the like can be varied in a wide range. In particular, the central group can be selected, if desired, so that, independently of the temperature dependence of the pitch and the threshold potential, the remaining properties of a mixture are not altered or are altered only immaterially.

Preferably, the groups $A^1$, $A^2$ and $A^3$ each are unsubstituted, cyano-, halogen- and/or methyl-substituted 1,4-phenylene; unsubstituted, cyano- and/or methyl-substituted trans-1,4-cyclohexylene; or one of the groups $A^1$, $A^2$ and $A^3$ also is pyridine-2,5-diyl, pyrazine-2,5-diyl, pyrimidine-2,5-diyl, pyridazine-3,6-diyl or trans-1,3-dioxane-2,5-diyl.

A preferred group of compounds of formula I comprises the optically active compounds of the formulae

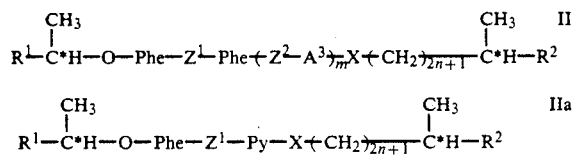

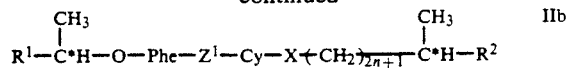

wherein Phe is unsubstituted, cyano-, halogen- and/or methyl-substituted 1,4-phenylene; Py is pyridine-2,5-diyl, pyrazine-2,5-diyl, pyrimidine-2,5-diyl or pyridazine-3,6-diyl; Cy is unsubstituted, cyano-, and/or methyl-substituted trans-1,4-cyclohexylene; and $R^1$, $R^2$, $Z^1$, $Z^2$, $A^3$, X, m, n and $C^*$ have the above significances.

In formula I and II above $A^3$ preferably stands for 1,4-phenylene, trans-1,4-cyclohexylene, pyridine-2,5-diyl, pyrazine-2,5-diyl, pyrimidine-2,5-diyl, pyridazine-3,6-diyl or trans-1,3-dioxane-2,5-diyl. It is especially preferred that A is 1,4-phenylene, trans-1,4-cyclohexylene or pyrimidine-2,5-diyl.

$Z^1$ in formula I and II above preferably is a single covalent bond, —COO— or —OOC—. $Z^2$ in formula I and II above preferably is a single covalent bond, —COO—, —OOC—, —$CH_2CH_2$—, —$CH_2O$— or —$OCH_2$—, especially a single covalent bond.

Py in formula IIa preferably stands for pyrimidine-2,5-diyl and Cy in formula IIb preferably stands for trans-1,4-cyclohexylene.

Especially preferred compounds are therefore the optically active compounds of the formula

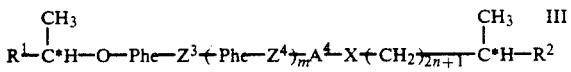

wherein $Z^3$ is a single covalent bond, —COO— or —OOC—; $Z^4$ denotes a single covalent bond, —COO—, —OOC—, —$CH_2CH_2$—, —$CH_2O$— or —$OCH_2$— or is especially preferred as a single covalent bond; $A^4$ represents 1,4-phenylene, trans-1,4-cyclohexylene or pyrimidine-2,5-diyl; and Phe, $R^1$, $R^2$, X, m, n and $C^*$ have the above significances.

Preferably, $Z^1$ or $Z^2$ in formula I and II, and $Z^3$ or $Z^4$ in formula III stand for a single covalent bond.

In general, there are preferred compounds of formula I, II, IIa, IIb and III with unsubstituted rings (that is, Phe preferably stands for 1,4-phenylene and Cy preferably stands for trans-1,4-cyclohexylene). However, if desired, the dielectric anisotrophy, the mesophase, the solubility and the like can be modified by using rings having cyano, halogen and/or methyl substituents.

Examples of preferred compounds of formula III are the optically active compounds of the formula

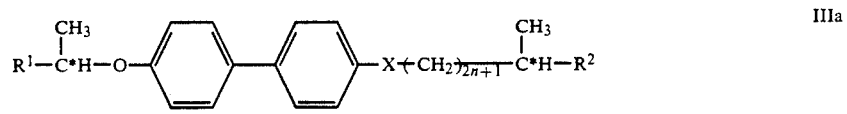

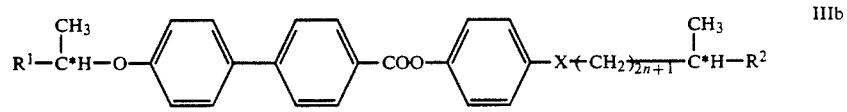

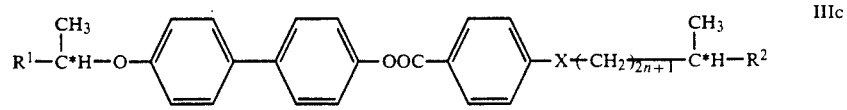

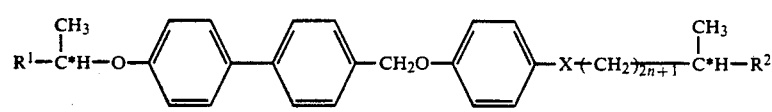
IIId
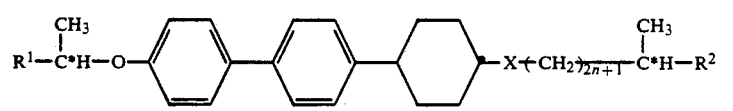
IIIe
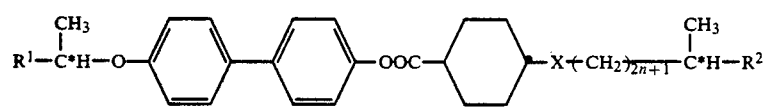
IIIf
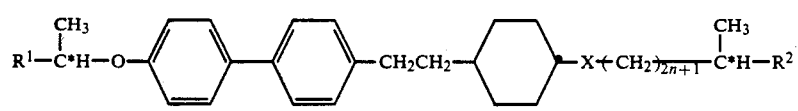
IIIg
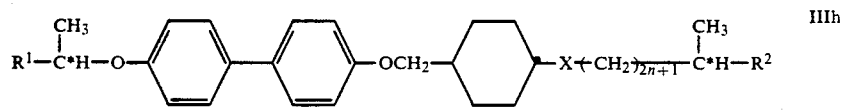
IIIh
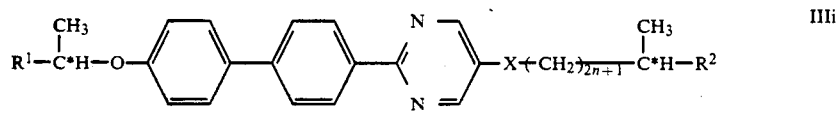
IIIi
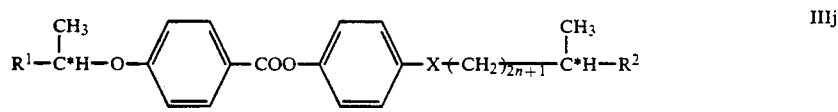
IIIj
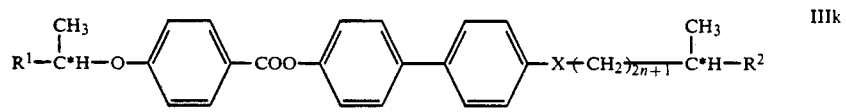
IIIk
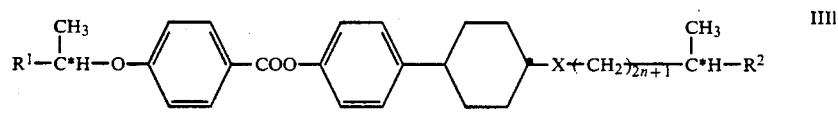
IIIl
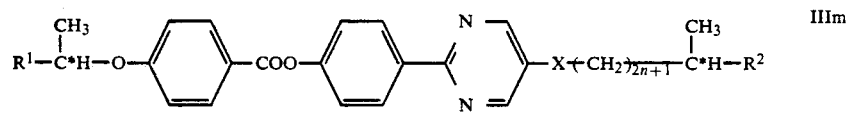
IIIm
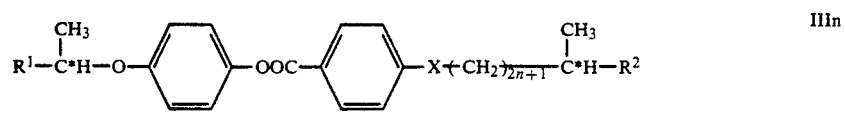
IIIn
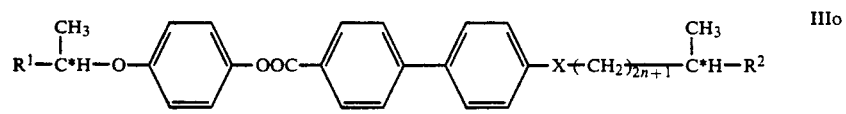
IIIo
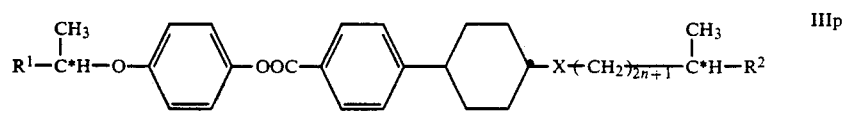
IIIp -continued

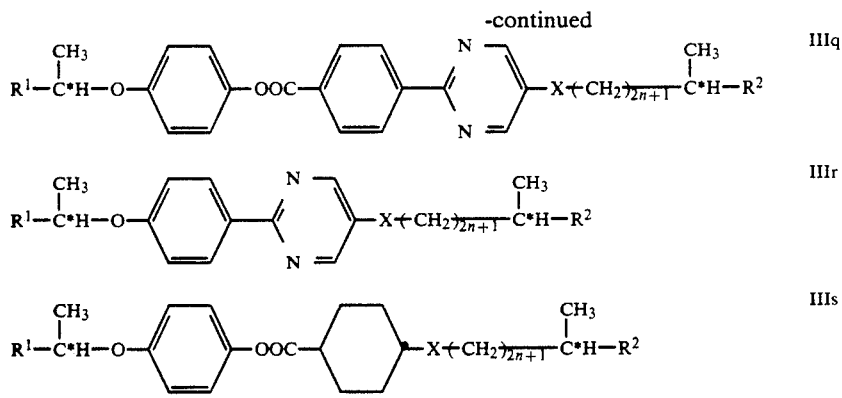

wherein R¹, R², X, n and C* have the above significances.

In the above formula I, II, IIa, IIb, III and IIIa-IIIs R¹ preferably stands for $C_3$-$C_{10}$-alkyl, preferably for a straight-chain alkyl such as propyl, butyl, pentyl, hexyl or heptyl, and R² preferably stands for $C_2$-$C_6$-alkyl, preferably for straight-chain alkyl such as ethyl, propyl or butyl. Those compounds in which R¹ is hexyl and R² is ethyl are in general especially referred. Further, n in formula I-III and IIIa-IIIs preferably stands for the number 0, 1 or 2.

The compounds in accordance with the invention can be prepared according to methods known per se. Suitable methods are well-known to a person skilled in the art, especially from the corresponding achiral compounds as well as from corresponding compounds having a chiral carbon atom. Suitable reagents for introducing the chiral end-group are also known from the preparation of the latter.

The compounds are especially preferred as components of liquid crystalline mixtures. The invention is therefore also concerned with a liquid crystalline mixture having at least 2 components, wherein at least one component is an optically active compound of formula I, especially one of the compounds referred to as being preferred.

The compounds have a pitch decreasing with increasing temperature in a wide temperature range. They can be used in nematic, cholesteric or smectic liquid crystal materials for influencing the temperature dependence of the pitch, especially for producing a pitch decreasing with increasing temperature or, for example, in combination with other chiral materials or chiral doping materials for producing an essentially temperature-constant pitch. The compounds in accordance with the invention can be used in principle in all known liquid crystal materials.

The amount of compounds of formula I in the mixtures can vary in wide limits depending on the range of application, the nature of the other components, the desired pitch or the desired temperature dependence of the pitch etc and can amount to, for example, about 0.1-50 wt. %.

Mixtures which contain one or more compounds of formula I and a nematic carrier material are especially preferred. Such mixtures are especially suitable for the temperature compensation of the threshold potential of indicating devices having a twisted nematic liquid crystal layer. The amount of compounds of formula I in these mixtures depends mainly on the desired pitch (typically about 5-500 μm) and on the desired temperature pattern of the pitch and in general amounts to about 0.1-10 wt. %, for example about 1-5 wt. %. If desired, the mixture can contain one or more additional chiral doping materials. The mixture conveniently has a positive dielectric anisotropy when used in TN-LCDS, STN-LCDS, SBE-LCDs or OMI-LCDs.

The invention is also concerned with an indicating cell having this mixture, namely a liquid crystal cell comprising a twisted nematic liquid crystal layer arranged between two plates, provided with electrodes and surface orientations, and polarizers, wherein the liquid crystal contains one or more compounds of formula I. The liquid crystal preferably has a positive dielectric anisotropy.

The mixtures and liquid crystal cells in accordance with the invention can be prepared in a manner known per se.

The invention is illustrated in more detail by the following Examples. The phases are denoted by the following symbols: C stands for crystalline, $S_C^*$ stands for chiral smectic C, Ch stands for cholesteric and I stands for isotropic.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees celsius (° C.), normal pressure is about 1 atmosphere, and room temperature is about 23° C. Examples were carried out as written unless otherwise indicated.

EXAMPLE 1

A mixture of 1.0 g of (R)-4-(1-methylheptyloxy)benzoic acid, 0.7 g of (S)-4-(2-methylbutyloxy)phenol, 1.0 g of N,N'-dicyclohexylcarbodiimide, 0.04 g of 4-(dimethyl-amino) pyridine and 50 ml of absolute dichloromethane was stirred at room temperature overnight. The mixture was subsequently filtered and concentrated. The crude product obtained was purified by chromatography on silica gel with toluene. The 4-[(R)-I-methylheptyloxy]benzoic acid 4-[(S)-2-methylbutyloxy]phenyl ester was distilled in a bulb-tube; cl.p. (Ch-I) −52° C.

The following compounds were prepared in an analogous manner:

4-[(R)-1-Methylheptyloxy]benzoic acid 4-[(S)-4-methyl-hexyloxy]phenyl ester, cl.p. (Ch-I) −33° C.;

4-[(R)-1-methylheptyloxy]benzoic acid 4-[(S)-6-methyloctyloxy]phenyl ester, cl.p. (Ch-I) −26° C.;

4-[(R)-1-methylheptyloxy]benzoic acid 4-[(S)-3-methyl-pentyl]phenyl ester, cl.p. (Ch-I) −61° C.;

4-[(R)-1-methylheptyloxy]benzoic acid 4'-[(S)-2-methylbutyloxy]-4-biphenylyl ester, m.p. (C-Ch) 62° C., transition $S_C^*$-Ch 52° C., cl.p. (Ch-I) 87° C.;

4-[(R)-1-methylheptyloxy)benzoic acid 4'-[(S)-3-methylpentyl]-4-biphenylyl ester, m.p. (C-I) 68° C., cl.p. (Ch-I) 65° C.;

4-(5-[(S)-5-methylheptyl]-2-pyrimidinyl)phenyl 4-[(R)-1-methylheptyloxy]benzoate, m.p. (C-I) 75° C., cl.p. (Ch-I) 49° C.;

trans-4-[(S)-3-methylpentyl)cyclohexanecarboxylic acid 4-[(R)-1-methylheptyloxy]phenyl ester, $[\alpha]^{22}_D = -0.004°$.

The following compounds can be prepared in an analogous manner:

4-[(R)-1-methylheptyloxy]benzoic acid 4-[(S)-8-methyl-decyloxy]phenyl ester;

4-[(R)-1-methylheptyloxy]benzoic acid 4-[(S)-10-methyl-dodecyloxy]phenyl ester;

4-[(R)-1-methylpropyloxy]benzoic acid 4-[(S)-2-methyl-butyloxy)phenyl ester;

4-[(R)-1-methylpropyloxy)benzoic acid 4-[(S)-4-methyl-hexyloxy)phenyl ester;

4-[(R)-1-methylpropyloxy]benzoic acid 4-[(S)-6-methyloctyloxy]phenyl ester;

4-[(R)-1-methylpropyloxy]benzoic acid 4-[(S)-8-methyl-decyloxy]phenyl ester;

4-[(R)-1-methylpropyloxy]benzoic acid-4-[(S)-10-methyl-dodecyloxy]phenyl ester;

4-[(R)-1-methylbutyloxy]benzoic acid 4-[(S)-2-methyl-butyloxy)phenyl ester;

4-[(R)-1-methylbutyloxy]benzoic acid 4-[(S)-4-methyl-hexyloxy]phenyl ester;

4-[(R)-1-methylbutyloxy]benzoic acid 4-[(S)-6-methyl-yl-octyloxy]phenyl ester;

4-[(R)-1-methylbutyloxy]benzoic acid 4-[(S)-B-methyldecyloxy]phenyl ester;

4-[(R)-1-methylbutyloxy]benzoic acid 4-[(S)-10-methyldodecyloxy)phenyl ester;

4-[(R)-1-methylheptyloxy]benzoic acid 4-[(S)-S-methyl-heptyl]phenyl ester;

4-[(R)-1-methylheptyloxy]benzoic acid 4-[(S)-7-methyl-nonyl]phenyl ester;

4-[(R)-1-methylheptyloxy]benzoic acid 4-[(S)-9-methyl-undecyl]phenyl ester;

4-[(R)-1-methylpropyloxy]benzoic acid 4-[(S)-3-methyl-pentyl]phenyl ester;

4-[(R)-1-methylpropyloxy]benzoic acid 4-[(S)-5-methyl-heptyl]phenyl ester;

4-[(R)-1-methylpropyloxy]benzoic acid 4-[(S)-7-methyl-nonyl]phenylester;

4-[(R)-1-methylpropyloxy)benzoic acid 4-[(S)-9-methyl-undecyl]phenyl ester;

4-[(R)-1-methylbutyloxy]benzoic acid 4-[(S)-3-methylpentyl)phenyl ester;

4-[(R)-1-methylbutyloxy]benzoic acid 4-[(S)-5-methyl-yl-heptyl]phenyl ester;

4-[(R)-1-methylbutyloxy]benzoic acid 4-[(S)-7-methyl-yl-nonyl]phenyl ester;

4-[(R)-1-methylbutyloxy]benzoic acid 4-[(S)-9-methyl-yl-undecyl]phenyl ester;

4-[(R)-1-methylheptyloxy]benzoic acid 4'-[(S)-4-methylhexyloxy]-4-biphenylyl ester;

4-[(R)-1-methylheptyloxy)benzoic acid 4'-[(S)-6methyloctyloxy]-4-biphenylyl ester;

4-[(R)-1-methylheptyloxy)benzoic acid 4'-[(S)-8-methyldecyloxy]-4-biphenylyl ester;

4-[(R)-1-methylheptyloxy]benzoic acid 4'-[(S)-10methyldodecyloxy]-4-biphenylyl ester;

4-[(R)-1-methylheptyloxy]benzoic acid 4'-[(S)-5-methylheptyl]-4-biphenylyl ester;

4-[(R)-1-methylheptyloxylbenzoic acid 4'-[(S)-7-methylnonyl)-4-biphenylyl ester;

4-[(R)-1-methylheptyloxy]benzoic acid 4'-[(S)-9-methylundecyl]-4-biphenylyl ester;

4-(5-[(S)-3-methylpentyl]-2-pyrimidinyl)phenyl 4-[(R)-1-methylheptyloxy)benzoate;

4-(5-[(S)-7-methylnonyl]-2-pyrimidinyl)phenyl 4-[(R)-1-methylheptyloxy]benzoate;

4-(5-[(S)-9-methylundecyl]-2-pyrimidinyl)phenyl 4-[(R)-1-methylheptyloxy)benzoate;

trans-4-[(S)-5-methylheptyl]cyclohexanecarboxylic acid 4-[(R)-1-methylheptyloxy]phenyl ester;

trans-4-[(S)-7-methylnonyl]cyclohexanecarboxylic acid 4-[(R)-I-methylheptyloxy]phenyl ester;

trans-4-[(S)-9-methylundecyl]cyclohexanecarboxylic acid 4-[(R)-1-methylheptyloxy]phenyl ester:

trans-4-[(S)-3-methylpentyl)cyclohexanecarboxylic acid 4'-[(R)-1-methylheptyloxy]-4-biphenylyl ester:

trans-4-[(S)-5-methylheptyl]cyclohexanecarboxylic acid 4'-[(R)-1-methylheptyloxyl-4-biphenylyl ester;

trans-4-[(S)-7-methylnonyl)cyclohexanecarboxylic acid 4'-[(R)-1-methylheptyloxy]-4-biphenylyl ester;

trans-4-[(S)-9-methylundecyllcyclohexanecarboxylic acid 4'-[(R)-1-methylheptyloxy]-4-biphenylyl ester;

as well as the optical antipodes of the named compounds, that is, those optical isomers in which in each case (R) is replaced by (S) and (S) is replaced by (R).

EXAMPLE 2

0.8 g of sodium hydroxide is dissolved in a solution of 5.09 g of 4'-[(S)-3-methylpentyl]-4-biphenylol (EP-A-131373) in 40 ml of ethanol. The solution is treated with 6.26 g of (S)-2-octyl-p-toluenesulfonate and heated to boiling for 6 hours. Subsequently, the solvent is distilled off and the residue is taken up in 100 ml of diethyl ether and 50 ml of 0.5 N hydrochloric acid. The aqueous phase is separated and back-extracted with 50 ml of diethyl ether. The combined organic phase is washed in succession with 50 ml of water, with 30 ml of 3 N sodium hydroxide solution and three times with 50 ml of water each time, then dried over sodium sulfate and concentrated. Crystallization of the residue from ethanol gives 4-[(R)-1-methylheptyloxy]-4'-(S)-3-methylpentyl]biphenyl, m.p. (C-I) 12° C.

The following compounds can be prepared in an analogous manner:

4-[(R)-1-Methylheptyloxy)-4'-[(S)-2-methylbutyloxyl-biphenyl, m.p. (C-I) 42° C.;

4-[(R)-1-methylheptyloxy]-4'-[(S)-4-methylhexyloxy]-biphenyl;

4-[(R)-1-methylheptyloxy]-4'-[(S)-6-methyloctyloxy]-biphenyl;

4-[(R)-1-methylheptyloxyl-4'-[(S)-B-methyldecyloxy]-biphenyl;

4-[(R)-1-methylheptyloxy]-4'-[(S)-10-methyl-
dodecyloxy]-biphenyl;
4-[(R)-1-methylheptyloxy]-4'-[(S)-5-methylheptyl]-
biphenyl;
4-[(R)-1-methylheptyloxy]-4'-[(S)-7-methylnonyl]-
biphenyl;
4-[(R)-1-methylheptyloxy]-4'-[(S)-9-methylundecyl]-
biphenyl;
5-[(S)-2-methylbutyloxy]-2-(4-[(R)-1-methylhep-
tyloxy)phenyl)pyrimidine;
5-[(S)-4-methylhexyloxy]-2-(4-[(R)-1-methylhep-
tyloxy)phenyl)pyrimidine;
5-[(S)-6-methyloctyloxy)-2-(4-[(R)-1-methylhep-
tyloxylphenyl)pyrimidine;
5-[(S)-8-methyldecyloxy]-2-(4-[(R)-1-methylhep-
tyloxy]phenyl)pyrimidine;
5-[(S)-10-methyldodecyloxy]-2-(4-[(R)-1-methylhep-
tyloxy]phenyl)pyrimidine;
5-[(S)-3-methylpentyl)-2-(4-[(R)-1-methylheptyloxy)-
phenyl)pyrimidine;
5-[(S)-5-methylheptyl]-2-(4-[(R)-1-methylheptyloxy]-
phenyl)pyrimidine, $[\alpha]^{22}_D = +0.060°$;
5-[(S)-7-methylnonyl]-2-(4-[(R)-1-methylheptyloxy)-
phenyl)pyrimidine;
5-[(S)-9-methylundecyl]-2-(4-[(R)-1-methylheptylox-
y]phenyl)pyrimidine;
as well as the optical antipodes of the named compounds, that is, those optical isomers in which in each case (R) is replaced by (S) and (S) is replaced by (R).

EXAMPLE 3

A nematic liquid crystal mixture (mixture A) was doped with a compound of formula I. The basic mixture and the doped cholesteric mixture (mixture B) were introduced into TN-LCDs with a liquid crystal layer thickness of 8 μm. The measurement of the threshold potentials $V_{90}$ for 90% transmission at various temperature gave the values compiled in Table 1:

| Mixture A: | |
|---|---|
| 7.10 wt. % of | 4'-ethyl-4-biphenylcarbonitrile, |
| 3.95 wt. % of | 4'-propyl-4-biphenylcarbonitrile, |
| 7.10 wt. % of | 4'-butyl-4-biphenylcarbonitrile, |
| 7.89 wt. % of | 4-(trans-4-propylcyclohexyl)benzonitrile, |
| 15.78 wt. % of | 4-(trans-4-pentylcyclohexyl)benzonitrile, |
| 16.57 wt. % of | 4-ethoxy-1-[2-(trans-4-propylcyclohexyl)-ethyl]benzene, |
| 4.73 wt. % of | 4-cyano-4''-pentyl-p-terphenyl, |
| 4.73 wt. % of | 4'-(trans-4-pentylcyclohexyl)-4-biphenyl-carbonitrile, |
| 11.05 wt. % of | 4-(trans-4-pentylcyclohexyl)-1-[2-(trans-4-butylcyclohexyl)ethyl]benzene, |
| 6.42 wt. % of | 4-ethyl-1-(trans-4-propylcyclohexyl)benzene, |
| 4.59 wt. % of | 4'-(trans-4-pentylcyclohexyl)-4-[2-(trans-4-butylcyclohexyl)ethyl]biphenyl, |
| 7.34 wt. % of | 4'-(trans-4-pentylcyclohexyl)-4-[2-(trans-4-butylcyclohexyl)ethyl]-1,1-ethylene-dibenzene, |
| 2.75 wt. % of | trans-4-[2-(trans-4-propylcyclohexyl)ethyl]-cyclohexanecarboxylic acid 4-cyanophenyl ester. |
| Mixture B: | |
| 97.73 wt. % of | mixture A, |
| 2.27 wt. % of | 4-[(R)-1-methylheptyloxy]benzoic acid 4-[(S)-2-methylbutyloxy]phenyl ester. |

TABLE 1

| Temperature (°C.) | Mixture A $V_{90}$ (Volt) | Mixture B $V_{90}$ (Volt) |
|---|---|---|
| −20 | 2.51 | 2.57 |
| −10 | 2.45 | 2.59 |
| 0 | 2.39 | 2.61 |
| 10 | 2.33 | 2.61 |
| 20 | 2.25 | 2.59 |
| 30 | 2.18 | 2.54 |
| 40 | 2.11 | 2.49 |
| 50 | 2.01 | 2.42 |

EXAMPLE 4

The above mixture A (from Example 3) was doped with various compounds of formula I and the temperature pattern of the natural pitch p of the cholestric mixture was investigated. The results are compiled in Table 2. Negative values of the pitch denote a left-handed twisting and positive values denote a right-handed twisting.

| Mixture C: | |
|---|---|
| 99 wt. % of | mixture A, |
| 1 wt. % of | 4-[(R)-1-methylheptyloxy]benzoic acid 4-[(S)-2-methylbutyloxy]phenyl ester; |
| m.p. < −40° C. | |
| Mixture D: | |
| 99 wt. % of | mixture A, |
| 1 wt. % of | 4-[(R)-1-methylheptyloxy]benzoic acid 4-[[(S)-4-methylhexyloxy]phenyl ester; |
| m.p. < −40° C. | |
| Mixture E: | |
| 99 wt. % of | mixture A, |
| 1 wt. % of | 4-[(R)-1-methylheptyloxy]benzoic acid 4-[(S)-6-methyloctyloxy]phenyl ester; |
| m.p. < −40° C. | |
| Mixture F: | |
| 99 wt. % of | mixture A, |
| 1 wt. % of | 4-[(R)-1-methylheptyloxy]benzoic acid 4-[(S)-3-methylpentyl]phenyl ester; |
| m.p. < −40° C. | |
| Mixture G: | |
| 99 wt. % of | mixture A, |
| 1 wt. % of | 4-(5-[(S)-5-methylheptyl]-2-pyrimidinyl)-phenyl 4-[(R)-1-methylheptyloxy]benzoate; |
| m.p. < −40° C. | |
| Mixture H: | |
| 99 wt. % of | mixture A, |
| 1 wt. % of | 4-[(R)-1-methylheptyloxy]-4'-[(S)-3-methylpentyl]biphenyl; |
| m.p. < −40° C. | |
| Mixture I: | |
| 99 wt. % of | mixture A, |
| 1 wt. % of | 4-[(R)-1-methylheptyloxy]-4'-[(S)-2-methylbutyloxy]biphenyl; |
| m.p. < −40° C. | |
| Mixture J: | |
| 99 wt. % of | mixture A, |
| 1 wt. % of | 5-[(S)-5-methylheptyl]-2-(4-[(R)-1-methylheptyloxy]phenyl)pyrimidine; |
| m.p. < −40° C. | |
| Mixture K: | |
| 99 wt. % of | mixture A, |
| 1 wt. % of | trans-4-[(S)-3-methylpentyl]cyclohexanecarboxylic acid 4-[(R)-1-methylheptyloxy]phenyl ester; |
| m.p. < −40° C. | |
| Mixture L: | |
| 99 wt. % of | mixture A, |
| 1 wt. % of | 4-[(R)-1-methylheptyloxy]benzoic acid 4'-[(S)-3-methylpentyl]-4-biphenylyl ester; |
| m.p. < −40° C. | |

TABLE

| Temperature (°C.) | Pitch p (μm) | | | | | | | | | |
|---|---|---|---|---|---|---|---|---|---|---|
| | Mixture C | Mixture D | Mixture E | Mixture F | Mixture G | Mixture H | Mixture I | Mixture J | Mixture K | Mixture L |
| −40 | −231.5 | −173.9 | −208.8 | −100.8 | −65.7 | −60.6 | −63.5 | −111.8 | −125.9 | −144.2 |
| −30 | −155.9 | −139.6 | −144.6 | −80.8 | −62.0 | −50.2 | −59.5 | −82.1 | −100.4 | −101.7 |
| −20 | −118.4 | −115.9 | −112.5 | −67.9 | −58.4 | −43.3 | −55.7 | −65.9 | −84.5 | −79.3 |
| −10 | −96.0 | −98.5 | −93.4 | −58.8 | −55.0 | −38.5 | −52.0 | −55.7 | −73.6 | −65.6 |
| 0 | −81.2 | −85.3 | −80.8 | −52.1 | −51.8 | −35.0 | −48.5 | −48.9 | −65.9 | −56.3 |
| 10 | −70.6 | −74.8 | −72.0 | −47.0 | −48.7 | −32.3 | −45.2 | −43.9 | −60.1 | −49.7 |
| 20 | −62.7 | −66.4 | −65.6 | −42.9 | −45.8 | −30.3 | −42.1 | −40.3 | −55.7 | −44.7 |
| 30 | −56.6 | −59.5 | −60.8 | −39.6 | −43.1 | −28.7 | −39.2 | −37.5 | −52.3 | −40.9 |
| 40 | −51.7 | −53.8 | −57.1 | −36.9 | −40.6 | −27.5 | −36.6 | −35.4 | −49.6 | −37.8 |
| 50 | −47.8 | −48.9 | −54.4 | −34.7 | −38.2 | −26.6 | −34.1 | −33.8 | −47.5 | −35.3 |
| 60 | −44.5 | −44.7 | −52.3 | −32.8 | −36.0 | −25.9 | −31.9 | −32.6 | −45.8 | −33.3 |

We claim:

1. An optically active compound of the formula:

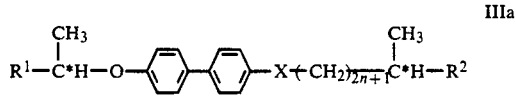
IIIa wherein $R^1$ and $R^2$ each are alkyl with at least 2 carbon atoms; n is an integer of 0 to 4; X is oxygen or a methylene group; and each of the two $C^*$ is a chiral carbon atom, one of the chiral carbon atoms having an R-configuration and another chiral carbon atom having an S-configuration.

2. The compound of claim 1 wherein $R^1$ is an $C_3$-$C_{10}$ alkyl group.

3. The compound of claim 1 wherein $R^1$ is a propyl, butyl, pentyl, hexyl or heptyl group.

4. The compound of claim 1 wherein n is the number 0, 1 or 2.

5. The compound according to claim 1, 4-4'-biphenyl.

6. The compound according to claim 1, 4-3-methylpentyl]biphenyl.

7. A liquid crystalline mixture having at least two components, wherein at least one component is an optically active compound of the formula:

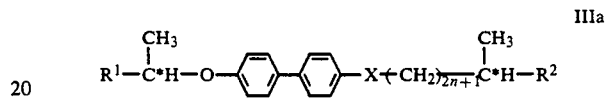
IIIa wherein $R^1$ and $R^2$ each are alkyl with at least 2 carbon atoms; n is an integer of 0 to 4; X is oxygen or a methylene group; and each of the two $C^*$ is a chiral carbon atom, one of the chiral carbon atoms having an R-configuration and another chiral carbon atom having an S-configuration.

8. The mixture of claim 7 further comprising a neumatic carrier material.

9. A liquid crystal cell comprising:
  a) two plate means,
  b) a liquid crystal means disposed between the two plate means and including a compound of formula:

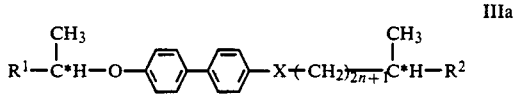
IIIa wherein $R^1$ and $R^2$ each are alkyl with at least 2 carbon atoms; n is an integer of 0 to 4; X is oxygen or a methylene group; and each of the two $C^*$ is a chiral carbon atom, one of the chiral carbon atoms having an R-configuration and another chiral carbon atom having an S-configuration; and
  c) means for applying an electrical potential to said plate means.

* * * * *

UNITED STATES PATENT AND TRADEMARK OFFICE
CERTIFICATE OF CORRECTION

PATENT NO. : 5,250,222
DATED : October 5, 1993
INVENTOR(S) : Stephen Kelly et al.

It is certified that error appears in the above-identified patent and that said Letters Patent is hereby corrected as shown below:

Col. 13, line 44,

In claim 5, delete 4-4'-biphenyl and add

"4-[(R)-1-methylheptyloxy]-4'-[(S)-2-methylbutyloxy]biphenyl."

Column 13, lines 45-46,

In claim 6, delete 4-3-methyl-pentyl]biphenyl and add

"4-[(R)-1-methylheptyloxy]-4'-[(S)-3-methylpentyl]biphenyl."

Signed and Sealed this

Sixteenth Day of May, 1995

Attest:

BRUCE LEHMAN

Attesting Officer     Commissioner of Patents and Trademarks